United States Patent
Freishtat

(10) Patent No.: US 8,057,795 B2
(45) Date of Patent: Nov. 15, 2011

(54) METHOD OF REDUCING THE ACTIVATION OF TH2 LYMPHOCYTES

(75) Inventor: Robert J. Freishtat, Potomac, MD (US)

(73) Assignee: Children's Research Institute, Washington, DC (US)

( * ) Notice: Subject to any disclaimer, the term of this patent is extended or adjusted under 35 U.S.C. 154(b) by 0 days.

(21) Appl. No.: 11/602,037

(22) Filed: Nov. 21, 2006

(65) Prior Publication Data

US 2008/0118516 A1 May 22, 2008

(51) Int. Cl.
*A61K 39/395* (2006.01)
*A61K 39/155* (2006.01)

(52) U.S. Cl. ................................. 424/144.1; 435/317.1

(58) Field of Classification Search .................. None
See application file for complete search history.

(56) References Cited

FOREIGN PATENT DOCUMENTS

WO   WO 2006/070286   *   7/2006

OTHER PUBLICATIONS

R & D Systems product Sheet, Monoclonal Anti-human NKG2A Antibody Catalog No. MAB1059, Published Jun. 26, 2007.*
Message and Johnston, The immunology of virus infection in asthma, 2001, European Respiratory Journal, vol. 18, pp. 1013-1025.*
Freishtat et al., T-Helper 2 Lymphocyte-Expressed NKG2A Suppresses Interleukin-4 Secretion Upon CD3/CD28/HLA-E Costimulation: A Novel Mechanism for T-Helper 2 Dominance in Asthma, 2006, Journal of Investigative Medicine, vol. 54, No. 2, p. S375.*
Noyola et al., Human metapneumovirus infections in Mexico: epidemiological and clinical characteristics, 2005, Journal of Medical Micbiology, vol. 54, pp. 969-974.*
Freishtat et al., Activated TH2 Lymphocytes Express NKG2A, -C and an NK-Like Phenotype, Mar. 2005, Journal of Investigative Medicine, vol. 53, Supplement No. 3, p. S396, paragraph 52.*
Catalog Number: FAB1059A, Monoclonal Anti-Human NKG2A-Allophycocyanin Clone # 131411, Apr. 2005, R&D Systems Product Information Sheet.*
Krug and Rabe, Animal Models for Human Asthma: The Perspective of a Clinician, 2008, Current Drug Targets, vol. 9, pp. 438-442.*
Gern, Chapter 7: Viral Respiratory Infections in Infancy and Chronic Asthma, 2009, Asthma and Infections, 1$^{st}$ Edition, Editors: Martin and Sutherland, pp. 111-122.*
Kawamura, H. et al. Amerlioration of acute graft-versus=host disease by NKG2A Engagement on Donor T Cells, Eur. J. Immunol. 35:2358 (2005).
Brooks, CR et al., Inhibitory Receptor NKG2A Determines Lysis of Vaccinia Virus,-Infected Autologous Targets by NK Cells J. Immunol. 11(2006).
Freishtat, RJ, et al. NKG2A and CD56 Are Expressed on Activated TH2 but not TH1 Lymphocytes, human Immunol. 66:1223 (2005).
Duma, M., et al. NK Cell Receptors Involved in the Response to Human CMV Infection, Curr. Top. Microbiol. Immunol. 298: 20.. (2006).
D'Andrea, et al., "Regulation of T Cell Lymphokine Production by Killer Cell Inhibitory Receptor Recognition of Self HLA Class I Alleles," The Journal of Experimental Medicine, Aug. 1996, pp. 789-794, vol. 184, The Rockefeller University Press, New York, NY, USA.

* cited by examiner

*Primary Examiner* — Mary E Mosher
*Assistant Examiner* — Benjamin P Blumel
(74) *Attorney, Agent, or Firm* — Blank Rome LLP

(57) ABSTRACT

We previously reported that NKG2A, a key inhibitory ligand for HLA-E, is expressed on activated TH2, but not TH1, cells. Here we measured cytokine expression in ex vivo TH2 cells and in a mouse model of asthma upon activation with antiCD3/28 and challenge with an NKG2A-specific agonist. We show that signaling through NKG2A modulates Th2 cell effector function. This new molecular pathway data provides a novel explanation and treatment for respiratory virus-associated asthma. RSV and hMPV suppress IFN-γ and HLA-E expression and therefore decrease NKG2A signaling in activated TH2 cells. This results in a relatively robust Th2 response and an unfavorable shift in Th1/Th2 balance. The data presented here suggest that increasing signaling via the NKG2A receptor suppresses Th2 effector function and could positively impact Th1/Th2 balance in asthma.

4 Claims, 3 Drawing Sheets

METHOD OF REDUCING THE ACTIVATION OF TH2 LYMPHOCYTES

SUPPORT ACKNOWLEDGEMENT

Figure 1:
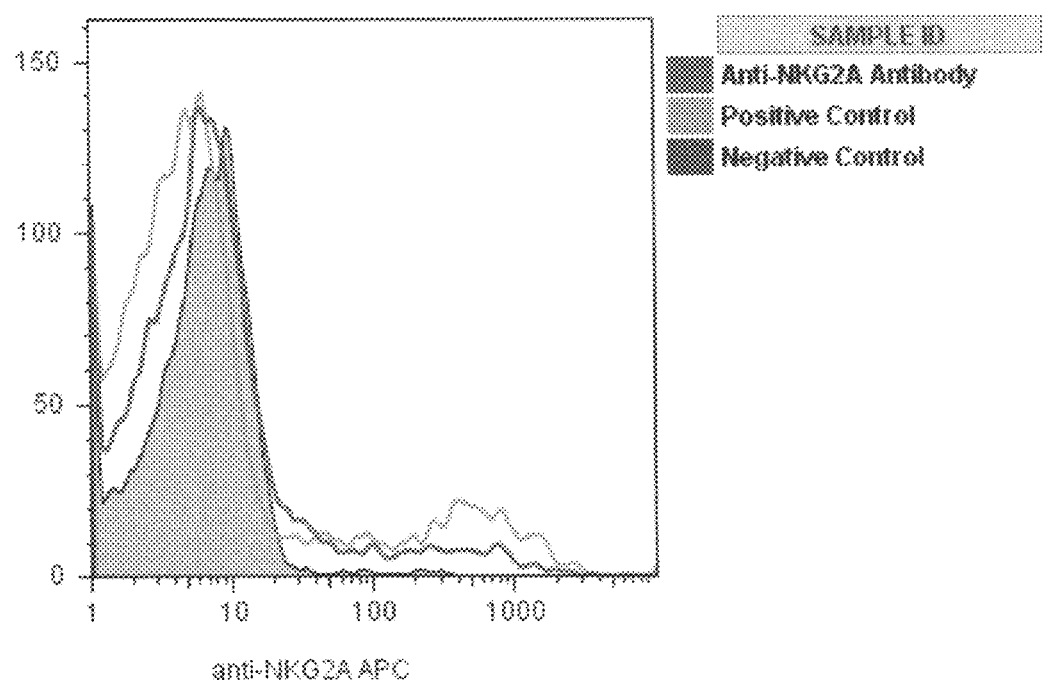

This research was supported by NIH grants K23-RR-020069 and M01-RR-020359. Consequently, the U.S. Government may have an interest in this invention.

FIELD OF THE INVENTION

The invention relates to the immunological treatment of viral-induced asthma. More specifically, it is directed to the treatment of asthmatics with an agonistic human monoclonal antibody to the NKG2A receptor protein of human Th2 lymphocytes.

BACKGROUND

Childhood asthma exacerbations are frequently associated with respiratory viral infections, more so than in adults[1-3]. Infectious agents such as rhinovirus, Respiratory Syncytial Virus (RSV), human metapneumovirus (hMPV), influenza virus, adenovirus, parainfluenza virus, and coronavirus are frequently identified in respiratory secretions from children with asthma exacerbations[4-9]. Several of these ensure their virulence via various means of immune evasion[10]. For example, RSV and hMPV have been shown to decrease interferon (IFN)-γ expression during acute infection[11-13] which limits the anti-viral cellular immune response. It is tempting to speculate that this type of immune evasion pathway is mechanistically coupled to asthma severity; however, until now, there has been little data to support this.

It is well established that T-helper type (Th2) cytokines predominate in asthma[14-16]. In a previous report, we found a potential molecular connection between respiratory virus-associated IFN-γ reduction and asthma-associated Th2 preponderance[17]. Specifically we found that NKG2A, a key protein receptor for the non-classical MHC class I antigen HLA-E[18-23], is expressed solely on activated Th2, but not Th1, cells[17]. IFN-γ acts at the HLA-E gene promoter to increase HLA-E expression[24]. Thus, we theorized that a viral-induced decrease in IFN-γ expression would result in a relative decrease in HLA-E expression. In turn, lower HLA-E expression would lead to less agonism at Th2 NKG2A receptors. The resultant decrease in NKG2A inhibitory signaling via its immunoreceptor tyrosine-based inhibition motif (ITIM) would lead to relatively increased Th2 cell effector function [25-28].

We previously hypothesized that activation of NKG2A receptors on Th2 cells would be expected to lead to downstream suppression of interleukin (IL)4 expression[17]. Here, we test this hypothesis using purified ex vivo Th2 cells with activation by anti-CD3/CD28 antibodies and challenge with an NKG2A-specific agonist monoclonal antibody, and by describing experiments with a mouse model of viral asthma.

SUMMARY OF THE INVENTION

We have found that signaling through the immunoinhibitory NKG2A receptor protein modulates Th2 cell effector function. This newly-discovered molecular pathway data provides a novel explanation for respiratory virus-associated asthma. Viruses suppress IFN-γ and HLA-E expression and therefore decrease NKG2A signaling in activated Th2 cells. This results in a relatively robust Th2 response and an unfavorable shift in Th1/Th2 balance. We have discovered that increasing signaling via the inhibitory NKG2A receptor with an agonist suppresses Th2 effector function and positively impacts Th1/Th2 balance in asthma.

In one example of the invention, the increased signaling of the NKG2A receptor protein is brought about by agonistic human antibodies directed to this receptor, and the result is protection against virus-induced asthma.

In another example, the agonistic antibody is a human monoclonal antibody.

In another representation of the invention, a mouse model of viral asthma is treated with a NKG2A agonistic monoclonal antibody that protects against asthma.

FIGURE LEGENDS

FIG. 1 shows a representative flow cytometry comparison of NKG2A expression for Th2 cells cultured with CD3/CD28 antibodies (positive control), CD3/CD28/NKG2A antibodies (human anti-NKG2A antibody), and culture medium alone (negative control) is shown. Analyses were gated by forward and side-scatter properties for live lymphocytes and on CD3+ CD4+ cells. We performed histogram smoothing and omitted the isotype control to allow for better visualization of the graph overlay.

Figure 2:
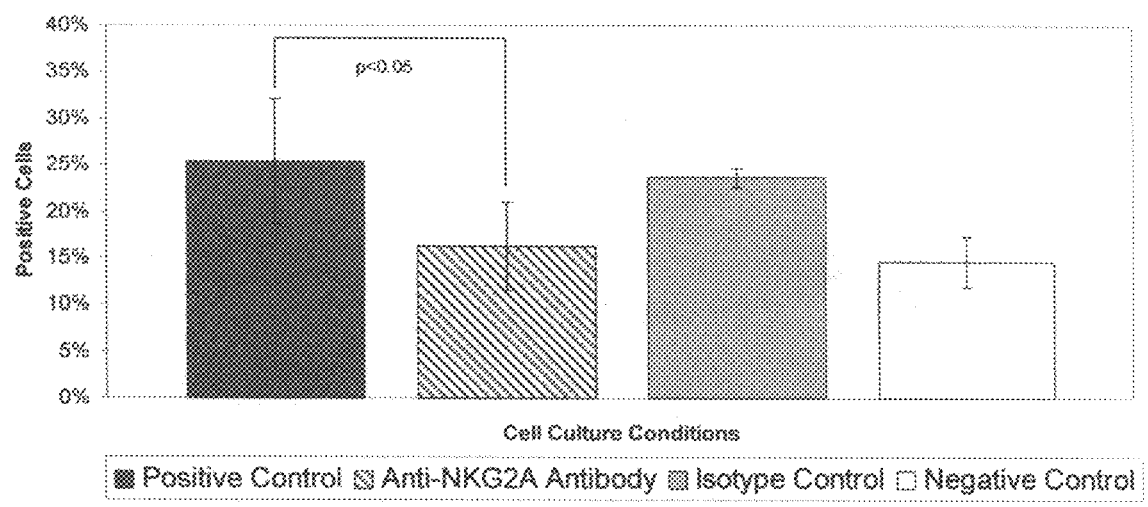

FIG. 2 shows a comparison of Th2 lymphocytes cultured in each of four culture conditions. Mean±SEM percent cells positive for IL-4 is shown in this graph.

Figure 3:
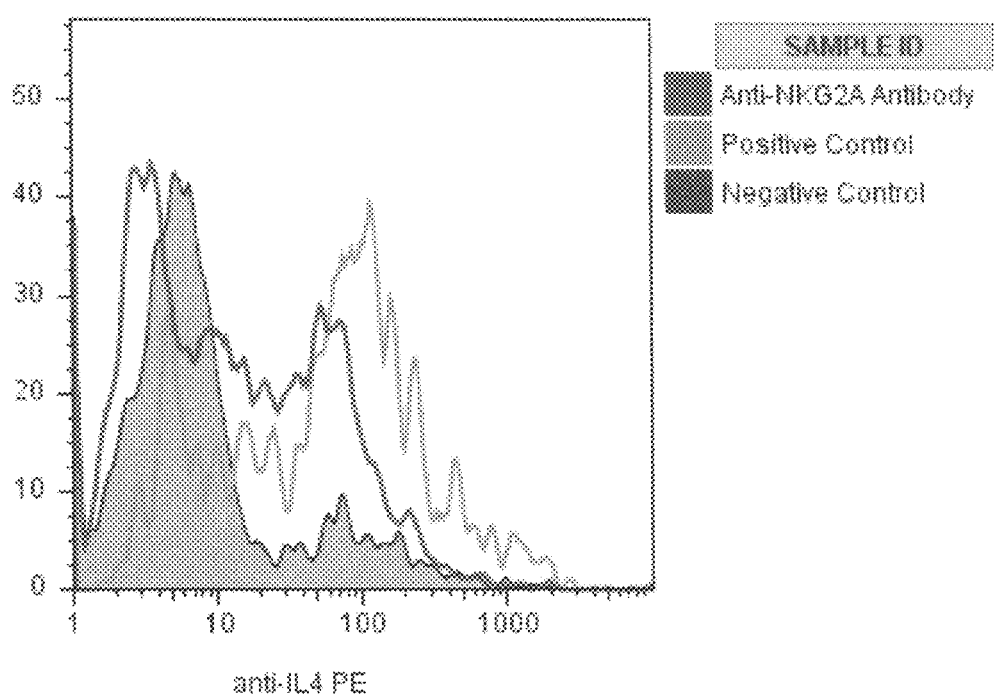

FIG. 3 shows flow cytometry comparison of IL-4 expression for an exemplary group of Th2 cells cultured with CD3/CD28 antibodies (positive control), CD3/CD28/NKG2A antibodies (human anti-NKG2A antibody), and $IgG_{2a}$ (isotype control). Analyses were gated by forward and side-scatter properties and on CD3+CD4+ cells. Here we performed histogram smoothing and omitted the isotype control to allow for better visualization of the graph overlay.

ABBREVIATIONS

RSV—Respiratory Syncytial Virus; hMPV—Human Metapneumovirus; HLA—Human Leukocyte Antigen; Th—T-Helper Cell; IL—Interleukin; IFN—Interferon; TCR—T Cell Receptor; PBMC—Peripheral Blood Mononuclear Cell

DETAILED DESCRIPTIONS OF THE PREFERRED EMBODIMENTS

We identified significant suppression of IL-4 expression in activated Th2 cells via NKG2A binding and ultimate TCR signaling inhibition. Extrapolated to a viral-induced asthma exacerbation scenario, where IFN-.gamma., HLA-E, and thus NKG2A binding are in low abundance, we have found that Th2 cells would exhibit a relatively robust response and that this response could potentially be modulated by an NKG2A agonist This represents a new aspect of Th1/Th2 balance in inflammation and has clinical implications in viral-exacerbated asthma. While the asthma-inducing virus used in experiments below is an adenovirus, the same treatment will be effective against asthma induced by other respiratory viruses, such as, respiratory syncytial virus, influenza virus, parainfluenza virus, coronavirus, and human metapneumovirus and adenovirus E 3119K (10-12).

The invention is described in both ex vivo and in vivo experiments.

Ex Vivo Experiments

Participants

Apparently healthy, non-atopic, non-asthmatic volunteers between the ages of 18 and 50 years had 60 ml of venous blood drawn directly into ethylenediaminetetraacetic acid (EDTA). The investigation was approved by the hospital's Institutional Review Board and General Clinical Research Center (GCRC) Advisory Committee and performed in the hospital GCRC.

TH2 Cell Isolation

Cell separation procedures were begun within 30 minutes of blood collection. Th2 cells were isolated from whole blood as we previously described [17 and U.S. patent application Ser. No. 11/471,417]. Briefly, EDTA-whole blood was centrifuged at low speed to allow removal of platelet-rich plasma. The remaining cells were diluted and centrifuged over Ficoll Paque PLUS™ (Amersham Biosciences, Piscataway, N.J.) density medium to isolate the peripheral blood mononuclear cell (PBMC) layer. The PBMCs were counted by hemocytometer to assure a concentration less than $8 \times 10^7$ cells/mL. Th2 lymphocytes were negatively isolated from the PBMCs using StemSep™ magnetic gravity columns (StemCell Technologies, Vancouver, BC) with a monoclonal antibody cocktail we previously validated for Th2

Cell Culture

Four cell culture conditions were used (Table 1), including combinations of resting and activated Th2 cells and challenge with an NKG2A agonist All Th2 cells, except negative controls, were pre-treated with $IgG_{2a}$ (R&D Systems, Minneapolis, Minn.) to prevent non-specific antibody binding. Plates for activated Th2 cell culture conditions were prepared with 10 µg/ml each of plate-bound anti-CD3 (Clone SK7: BD Biosciences, San Diego, Calif.) and suspended anti-CD28 antibodies (Clone 15E8: Chemicon International/Upstate USA, San Francisco, Calif.). The enriched Th2 cells ($<1 \times 10^6$ cells/mL) were aliquoted equally into each of the four cell culture conditions suspended in HB 101 Basal Media (Irvine Scientific, Santa Ana, Calif.), 10% HB Basal Supplement (Irvine Scientific), 10% autologous plasma, 10% Penicillin/Streptomycin (Sigma-Aldrich, St Louis, Mo.), and 1% Gentamicin (Sigma-Aldrich). Negative control wells contained Th2 cells in culture media alone.

Several NKG2A agonists are suitable for use. Among these are human antibodies and human monoclonal antibodies. For example, one such is human anti-NKG2A monoclonal antibody (clone 131411, R&D Systems, California) that specifically binds the NKG2A receptor and elicits its inhibitory signal [29, 30]. Another suitable antibody is the anti-NKG2A/C/E human monoclonal antibody (clone 20d5, used by Kawamura et al. [32]). Cells were treated with 10 µg/ml of anti-NKG2A monoclonal antibody at culture inception and every 24 hours. Likewise, isotype control cells were treated every 24 hours with 10 µg/ml of anti-$IgG_{2a}$ (R&D Systems, CA), the isotype for the ant-NKG2A antibody. All cell culture conditions were maintained for 48 hours at 37° C. and 5% $CO_2$.

Flow Cytometry

Post-culture Th2 cells underwent a series of incubations with fluorescent-labeled monoclonal antibodies, as well as permeablization and fixation with 2% paraformaldehyde. Four-color flow cytometry (FACSCalibur™ System, BD) was performed with varying combinations of anti-CD3-PerCP (BD), anti-CD4-FITC (BD), anti-CD4-APC (BD), anti-NKG2A-APC (R&D Systems), anti-NKG2C-PE (R&D Systems), anti-IFN-γ-FITC (BD), and anti-IL-4-PE (BD) using appropriate isotype and negative (unlabeled cells) controls. Cells were gated for viable Th2 lymphocytes using forward- and side-scatter properties and CD3+CD4+ double positivity. Flow data were analyzed with FlowJo 7.1 (Tree Star, Inc., Ashland, Oreg.).

Data Analysis

Within- and between-culture condition comparisons were made for percent positive cells, geometric mean fluorescence intensity (MFI), and net MFI. Statistical significance was tested with SPSS 13 (SPSS, Chicago, Ill.) using paired T-tests. The results are shown and discussed in examples 1 and 2 below.

In Vivo Experiments

Our hypothesis is that viral-induced reductions in Th1 cellular and cytokine activity lead to a relative increase in Th2 activity in a mouse model of asthma. Further, we hypothesize that NKG2A signaling can be used in these mice to moderate the Th2 response. To that end, a two-phase experiment may be carried out.

First, experiments may be done with Jackson Laboratories' B6.129S6-Tbx21$^{tm1Glm}$J mice. Mice that are homozygous for the targeted mutation are viable, fertile and normal in size. No gene product (mRNA or protein) is detected in isolated lymph node T cells by Northern or Western blot analysis. T cells from the homozygotes do not produce the Th1-type cytokine interferon gamma and secrete elevated levels of Th2-type cytokines in response to in vitro T cell receptor (TCR) cross-linking and in vivo protein antigen immunization. Additionally, mice homozygous for the targeted mutation on this genetic background are susceptible to *Leishmania major* infections. Without induced sensitization or challenge, female homozygotes display hyper-responsiveness (AHR) with resulting airway remodeling similar to characteristics of asthma. Histological analysis of lung tissue from female homozygous mice, aged 4 to 6 weeks, reveals eosinophil and lymphocyte infiltration of peribronchial and perivenular tissue, thickening of the subepithelial collagen layer, and increased numbers of myofibroblast cells in bronchial tissue. Bronchial alveolar lavage fluid contains elevated levels of TGFB1 (TGF-beta 1), TNF (TNF-alpha), IL4 and IL13. Mice heterozygous for the targeted mutation display an intermediate phenotype. This mutant mouse strain represents a model that may be useful in studies of acute and chronic human asthma and chronic intestinal inflammation (Information taken from Jackson Laboratories web site). Homozygotes do not produce the Th1 cytokines and secrete elevated levels of Th2 cytokines in response to in vivo protein antigen immunization. Mice may be sensitized with ovalbumin following pre-treatment with anti-NKG2A monoclonal antibody, and. reductions in Th2 cytokines and airway hyperresponsiveness may be measured as an reflection of a reduction in asthma symptoms.

Second, standard Balb-c/J mice may be infected with respiratory syncytial virus or human metapnuemovirus following pretreatment with anti-NKG2A monoclonal antibody. Reductions in Th2 cytokines and airway hyperresponsiveness may be measured.

EXAMPLES

Example 1

A total of eight apparently healthy, non-atopic, non-asthmatic adult volunteers were enrolled in this study. Both genders and a diverse group of ethnicities and races were represented among the participants.

Following culture in the four distinct conditions (positive control, anti-NKG2A antibody, isotype control, and negative control) Th2 cell samples were examined by four-color flow cytometry to confirm the expected rise in cells positive for NKG2A surface expression. The cultured cells were >97% pure CD3+CD4+CD8– Th cells. We found significant up-regulation of Th2 NKG2A positivity from 7.3±2.3% in negative controls to 13.7±3.8% in positive controls (p=0.03) consistent with our previously published data[17]. (Table 2 and FIG. 1) There was no significant difference in the surface expression of NKG2A (16.0±4.0%) on the activated Th2 cells cultured in the presence of anti-NKG2A antibodies and the positive controls. Additionally, there was no appreciable change in the low level expression of activating NKG2C. This was also consistent with our previous findings[17].

Example 2

In order to assess the impact of NKG2A signaling on Th2 cell effector function following activation through the TCR, we performed flow cytometry for intracellular expression of IL-4 and IFNγ. There was significant up-regulation of intracellular IL-4 from 16.1±3.2% in negative controls to 25.4±6.7% in positive controls (p=0.03). (Table 3 and FIG. 2) When TH2 cells were activated in culture in the presence of anti-NKG2A antibodies, the intracellular expression of IL-4 fell from 25.4±6.7% to 16.3±4.7% (p=0.05). (Table 3 and FIG. 3) This level of IL-4 expression was not significantly different from the negative controls (14.6±3.7%).

We also examined expression of IFN-γ and found similar changes in intracellular expression. Negative control expression was 4.8±0.8%. (Table 3) This increased to 7.7±1.3% in positive controls (p=0.05) and fell to 5.5±1.3% in the presence of anti-NKG2A antibody (p=0.04). This level of expression was not different from negative controls.

Discussion of Results

Advancing the understanding of Th2 preponderance in asthma is fundamental to improving treatment. Using a monoclonal antibody cocktail we developed for the negative isolation of human Th2 cells, we confirmed our previous work showing a significant increase in NKG2A surface protein expression following the activation of Th2 cells [17]. Here, we tested the hypothesis that activated Th2 cell effector function is diminished in the presence of NKG2A signaling, with a consequent killing of respiratory viruses that cause bronchial asthma.

We induced NKG2A signaling using human monoclonal antibodies specific for the NKG2A receptor that has been shown to be an agonist and cause suppression of NK cell cytotoxicity in P815 target cells [30]. We used a magnetic gravity column isolation to obtain quiescent human peripheral blood Th2 cells (99% CD3+/CD4+ by flow cytometry and 84% pure Th2 cells by T-bet:GATA-3 mRNA ratio[17]) These Th2 cells were activated with the NKG2A agonist antibody and then studied for downstream signaling of IL-4. Activated Th2 cells cultured with this NKG2A agonist showed a significant decrease in effector function as measured by intracellular IL-4 expression by FACS. As NKG2A is expressed on Th2 but not Th1 cells [17], our activation of NKG2A would have the functional consequence of altering Th1/Th2 cytokine ratios. To our knowledge, this is the first ex vivo immune modulation of human Th2 cells.

The data presented here indicate that use of such NKG2A agonist antibodies could modulate Th1/Th2 balance in a positive direction and thus suppress inflammatory responses of asthma. Consistent with this model, Kawamura, et al. used anti-NKG2A monoclonal antibodies to restrict donor T cell expansion and suppress inflammation in a murine model of acute graft-versus-host disease [34]. Our data suggest that this may also be possible in human diseases like asthma, colitis, and autoimmune diseases where Th1/Th2 cell and cytokine balance is important The finding that the NKG2A receptor is capable of modulating Th2 cell effector function is analogous to its purpose on CD8+ cytotoxic T cells, where it helps prevent cytotoxicity of HLA-E expressing cells. In Th2 cells it appears that there is concomitant binding of NKG2A to HLA-E along with the CD4+-TCR to MHC class II. This parallel receptor-ligand binding results in transmission of an inhibitory signal from NKG2A via SHP-2 along with the activating signal from the TCR. In the situation of RSV and hMPV infections, where lymphocytes are activated but IFN-γ and HLA-E expression are decreased [35, 36], NKG2A inhibition of Th2 effector function would be relatively decreased despite up-regulation of NKG2A surface expression. This would lead to a relatively robust Th2 response.

REFERENCES

1. Murray C S et al: Allergens, Viruses, and Asthma Exacerbations. Proc Am Thorac Soc 1(2):99, 2004.
2. Johnston S L, et al. Community study of role of viral infections in exacerbations of asthma in 9-11 year old children. Brit Med J 310(6989):1225, 1995.
3. Nicholson K G, et al.: Respiratory viruses and exacerbations of asthma in adults. Brit Med J 307(6910):982, 1993.
4. Chiu S S, et al.: Human coronavirus NL63 infection and other coronavirus infections in children hospitalized with acute respiratory disease in Hong Kong, China. Clin Infect Dis 40(12):1721, 2005.
5. Foulongne V, et al.: Human metapneumovirus infection in young children hospitalized with respiratory tract disease. Pediatr Infect Dis J 25(4):354, 2006.
6. Kling S, et al.: Persistence of rhinovirus RNA after asthma exacerbation in children. Clin Exp Allergy 35(5):672, 2005.
7. Matsuse H, et al.: Naturally occurring parainfluenza virus 3 infection in adults induces mild exacerbation of asthma associated with increased sputum concentrations of cysteinyl leukotrienes. Int Arch Allergy Immunol 138(3):267, 2005.
8. Murray C S, et al.: Study of modifiable risk factors for asthma exacerbations: virus infection and allergen exposure increase the risk of asthma hospital admissions in children. Thorax 61(5):376, 2006.
9. Xatzipsalti M, et al.: Rhinovirus viremia in children with respiratory infections. Am J Respir Crit Care Med 172(8):1037, 2005.
10. Hewitt E W: The MHC class I antigen presentation pathway: strategies for viral immune evasion. Immunology 110(2):163, 2003.
11. Kaneko H, et al: Suppression of IFN-gamma production in atopic group at the acute phase of RSV infection. Pediatr Allergy Immunol 17(5):370, 2006.
12. Douville R N, et al.: Human Metapneumovirus Elicits Weak IFN-{gamma} Memory Responses Compared with Respiratory Syncytial Virus. J Immunol 176(10):5848, 2006.
13. Aberle J H, et al: Reduced Interferon-gamma Expression in Peripheral Blood Mononuclear Cells of Infants with Severe Respiratory Syncytial Virus Disease. Am. J. Respir. Crit Care Med. 160(4):1263, 1999.

14. Campbell J J, et al.: Expression of chemokine receptors by lung T cells from normal and asthmatic subjects. Journal of Immunology 166(4):2842, 2001.
15. Heaton T, et al.: An immunoepidemiological approach to asthma: identification of in-vitro T-cell response patterns associated with different wheezing phenotypes in children. Lancet 365(9454):142, 2005.
16. Robinson D S, et al.: Predominant TH2-like bronchoalveolar T-lymphocyte population in atopic asthma. New England Journal of Medicine. 326(5):298, 1992.
17. Freishtat R J, et al.NKG2A and CD56 are coexpressed on activated TH2 but not TH1 lymphocytes. Hum Immunol 66(12):1223, 2005.
18. Posch P E, et al.: HLA-E is the ligand for the natural killer cell CD94/NKG2 receptors. J Biomed Sci 5(5):321, 1998.
19. Braud V M, et al.: HLA-E binds to natural killer cell receptors CD94/NKG2A, B and C. Nature 391(6669):795, 1998.
20. Brooks A G, et al.: Specific recognition of HLA-E, but not classical, HLA class I molecules by soluble CD94/NKG2A and NK cells. J Immunol 162(1):305, 1999.
21. Lee N, et al.: HLA-E is a major ligand for the natural killer inhibitory receptor CD94/NKG2A. Proc Natl Acad Sci USA 95(9):5199, 1998.
22. Maier S, et al.: Implications of HLA-E allele expression and different HLA-E ligand diversity for the regulation of NK cells. Hum Immunol 61(11):1059, 2000.
23. Miller J D, et al. Analysis of HLA-E peptide-binding specificity and contact residues in bound peptide required for recognition by CD94/NKG2. J Immunol 171(3):1369, 2003.
24. Barrett D M, et al.: A GATA factor mediates cell type-restricted induction of HLA-E gene transcription by gamma interferon. Mol Cell Biol 24(14):6194, 2004.
25. Houchins J P, et al.: Natural killer cell cytolytic activity is inhibited by NKG2-A and activated by NKG2-C. J Immunol 158(8):3603, 1997.
26. Borrego F, et al.NKG2A inhibitory receptors are internalized and recycle independently of inhibitory signaling processes. J Immunol 169(11):6102, 2002.
27. Braud V M, et al. Expression of CD94-NKG2A inhibitory receptor is restricted to a subset of CD8+ T cells. Trends Immunol 24(4):162, 2003.
28. Kabat J, et al.: Role that each NKG2A immunoreceptor tyrosine-based inhibitory motif plays in mediating the human CD94/NKG2A inhibitory signal. J Immunol 169(4):1948, 2002.
29. Brando C, et al.: Receptors and lytic mediators regulating anti-tumor activity by the leukemic killer T cell line TALL-104. J Leukoc Biol 78(2):359, 2005.
30. Monoclonal Anti-human NKG2A Antibody. vol 2006.
31. Zheng W, et al.: The transcription factor GATA-3 is necessary and sufficient for Th2 cytokine gene expression in CD4 T cells. Cell 89:587-596, 1997.
32. Marusina Al, et al. GATA-3 is an important transcription factor for regulating human NKG2A gene expression. J Immunol 174(4):2152, 2005.
33. Romero P, et al., Santamaria M: Expression of CD94 and NKG2 molecules on human CD4(+) T cells in response to CD3-mediated stimulation. J Leukoc Biol 70(2):219, 2001.
34. Kawamura H, et al.: Amelioration of acute graft-versus-host disease by NKG2A engagement on donor T cells. Eur J Immunol 35(8):2358, 2005.
35. Lopez-Botet M, et al. surveillance of HLA class I expression: a paradigm of host-pathogen adaptation. Immunol Rev 181:193, 2001.
36. Wu J, et al.: Intracellular retention of the MHC class I-related chain B ligand of NKG2D by the human cytomegalovirus UL16 glycoprotein. J Immunol 170(8):4196, 2003.
37. Labonte M L, et al.: Variable NKG2 expression in the peripheral blood lymphocytes of rhesus monkeys. Clin Exp Immunol 138(2):205, 2004.

TABLE 1

Description of Cell Culture Conditions

| Condition | Cell Stimulants (10 µg/mL each) | Added Antibody* (10 µg/mL each) |
|---|---|---|
| Positive Control | anti-CD3 and anti-CD28 | None |
| Anti-NKG2A Antibody | anti-CD3 and anti-CD28 | anti-NKG2A |
| Isotype Control | anti-CD3 and anti-CD28 | $IgG_{2a}$ |
| Negative Control | None | None |

*Added every 24 hours.

TABLE 2

Between Cell Culture Condition Comparisons of TH2 Cell Positivity for NKG2A

| Condition | | NKG2A | NKG2A MFI |
|---|---|---|---|
| Positive Control | Mean | 13.7% | 19.02 |
| | SEM | 3.8% | 9.43 |
| | p-value (Negative Control) | 0.034 | 0.02 |
| Anti-NKG2A Antibody | Mean | 16.0% | 21.81 |
| | SEM | 4.0% | 7.79 |
| | p-value (Positive Control) | 0.172 | 0.14 |
| | p-value (Negative Control) | 0.025 | 0.02 |
| Negative Control | Mean | 7.3% | 6.91 |
| | SEM | 2.4% | 0.78 |
| | p-value | — | — |

$p \leq 0.05$ in bold.

TABLE 3

Between Cell Culture Condition Comparisons of Th2 Cell Positivity for IL-4 and IFN-γ

| Condition | | IL-4 Positive (%) | Fold IL-4 MFI | IFNγ Positive (%) | Fold IFNγ MFI |
|---|---|---|---|---|---|
| Positive Control (CD3/CD28) | Mean | 25.4% | 7.98 | 7.7% | 7.43 |
| | SEM | 6.7% | 1.91 | 1.3% | 1.42 |
| | p-value (Negative Control) | 0.03 | 0.07 | 0.05 | 0.05 |
| | p-value (Isotype Control) | 0.12 | 0.15 | 0.35 | 0.24 |
| Anti-NKG2A Antibody (CD3/CD28 + anti-NKG2A) | Mean | 16.3% | 6.43 | 5.5% | 5.29 |
| | SEM | 4.7% | 1.92 | 1.3% | 1.50 |
| | p-value (Positive Control) | 0.05 | 0.02 | 0.04 | 0.01 |
| | p-value (Isotype Control) | 0.09 | 0.26 | 0.43 | 0.23 |
| Isotype Control (CD3/CD28 + IgG2a) | Mean | 23.7% | 7.81 | 4.9% | 6.50 |
| | SEM | 1.0% | 0.72 | 2.7% | 0.43 |
| | p-value | — | — | — | — |
| Negative Control (Culture Medium Alone) | Mean | 16.1% | 5.95 | 4.8% | 4.83 |
| | SEM | 3.2% | 1.78 | 0.8% | 1.60 |
| | p-value | — | — | — | — |

$p \leq 0.05$ in bold.

I claim:

1. A method for reducing Th2 lymphocyte activation, comprising the step of contacting Th2 lymphocytes with an effective amount of an agonist, which is an antibody, directed to the NKG2A receptor protein of the Th2 lymphocytes.

2. The method of claim 1, wherein said antibody is a human antibody.

3. The method of claim 2, wherein said human antibody is a human monoclonal antibody.

4. The method of claim 3, wherein said human monoclonal antibody is selected from the group consisting of Clone 131411 and Clone 20d5.

* * * * *